United States Patent [19]

Barfknecht et al.

[11] 4,000,197
[45] Dec. 28, 1976

[54] ASYMMETRIC SYNTHESIS OF PHENYLISOPROPYLAMINES

[75] Inventors: Charles F. Barfknecht; David E. Nichols, both of Iowa City, Iowa

[73] Assignee: The University of Iowa Research Foundation, Iowa City, Iowa

[22] Filed: July 23, 1973

[21] Appl. No.: 381,466

[52] U.S. Cl. .................. 260/570.8 R; 260/559 R; 260/566 F; 260/592; 260/612 D
[51] Int. Cl.² ........................................ C07C 87/28
[58] Field of Search .......... 260/570.8 R, 592, 501.1

[56] References Cited

UNITED STATES PATENTS

| | | | |
|---|---|---|---|
| 2,146,475 | 2/1939 | Hildebrandt | 260/570.8 |
| 2,223,686 | 12/1940 | Hildebrandt | 260/570.8 |
| 3,689,524 | 9/1972 | Jack et al. | 260/570.8 X |

OTHER PUBLICATIONS

Weinges et al.; "Chem. Ztg. Chem. App.", vol. 94, No. 19, p. 728 (1970).
Adams et al., "Organic Reactions", vol. IV, pp. 181–182, 189–195, 223 and 236, (1948).

*Primary Examiner*—Robert V. Hines
*Attorney, Agent, or Firm*—Beveridge, DeGrandi, Kline & Lunsford

[57] ABSTRACT

The synthesis of enantiomers of a series of methoxy- and alkyl- substituted phenylisopropylamines is described. The synthesis comprises reducing the imines, formed by the reaction of appropriate phenylacetones with either (+)- or (−)-α-methylbenzylamine, by low-pressure reduction techniques, and subsequently subjecting the optically active N-(α-phenethyl)phenylisopropylamine derivative to hydrogenolysis. The hydrogenolysis products are characterized by enantiomeric purities in the range of 96 – 99%. Yields of products are approximately 60%.

22 Claims, No Drawings

ASYMMETRIC SYNTHESIS OF PHENYLISOPROPYLAMINES

The invention described herein was made in the course of work under a grant or award from the Department of Health, Education, and Welfare.

DESCRIPTION

The invention is directed to the synthesis of compounds of the formula

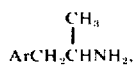

and salts thereof. The symbol "Ar" is used herein to designate phenyl or phenyl substituted by selected groups as defined in greater detail hereinafter. More specifically, the invention is directed to the asymmetric synthesis of these compounds particularly the (S)-(+) and the (R)-(−) enantiomers. The compounds of the invention are conventionally classified as amphetamine derivatives. Amphetamine is phenylisopropylamine.

In an article published by C. F. Barfknecht, and D. E. Nichols, published in the *Journal of Medicinal Chemistry*, Volume 15, page 109 (1972), it was suggested that LSD could be considered a phenethylamine derivative. LSD is a lysergic acid alkaloid. Natural lysergic acid, of the formula

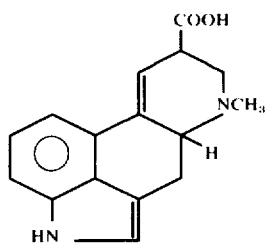

possesses the 5R,8R absolute configuration, established by H. G. Leeman and S. Fabbri, in *Helv. Chim. Acta*, 42, 2696 )1959) and P. Stadler and A. Hofmann, ibid., 45, 2005 (1962). The absolute configuration of phenylisopropylamines, or amphetamines, are S-(+) (I) and R-(−) (II) as determined by P. Karrer and E. Ehrhardt, in *Helv. Chim. Acta*, 34 2202 (1951).

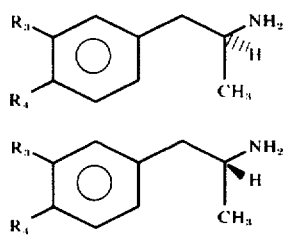

It was predicted that the psychotomimetic effects of the amphetamines might reside in the R enantiomers, based on their stereochemical relationship to lysergic acid.

While much information was available in the prior art about the structural activity relationships of one-ring psychotomimetics, only recently have research groups reported data on the relative potency of optical isomers of the 1-ring psychotomimetics.

The psychotomimetic effects of (+)-3,4-dimethoxy phenylisopropylamine and (−)-3,4-dimethoxy phenylispropylamine and of (+) amphetamine were determined in studies on rats and published in the *Journal of Medicinal Chemistry*, Volume 15, 109 (1972). p-methoxy phenylisopropylamine has been shown to exhibit "LSD-like" potency in rats, in a publication by Smythies et al. in Nature 216:128 (1967). The comparative effects of the stereoismers of P-methoxyamphetamine, or P-metoxyphenylisopropylamine, were studied in the manuscript submitted for publication entitled "Comparative Effects of Stereo Isomers of Psychotomimetic Amphetamines" by Dyer et al. The phychotomimetic effects of 2,4- and 2,5-dimethoxy-phenylisopropylamines was studied by Shulgin et al. and published in Nature 221:357 (1969). Peretz reported that 3,4,5-dimetoxy-4-bromoamphetamines was hallucinogenic in man. 2,5-Dimethoxy-4-methyl substituted phenyl isopropyl amine has been the subject of research, which has revealed that the R-(+) enantiomer is responsible for the sensory and halucinatory effects of 2,5-dimethoxy-4-methylamphetamine, which results were published by Shulgin, *J. Pharm. Pharmacol*, in press.

Weingartner et al. have published experimental data relating to the psychotomimetic effects of 2,5-dimethoxy-4-ethylamphetamines, in *Behavioral Science*, Volume 15, No. 4, July, 1970. Bennington et al. in unpublished results, have observed that the R-(−) isomer is also responsible for the psychotomimetic effects of 2,5-dimethoxy-4-bromoamphetamine, first disclosed by Barfknecht and Nichols in the *Journal of Medicinal Chemistry*, 14, 370 (1971) and A. T. Shulgin et al. in *Pharmacology*, 5, 103 (1971).

All of the foregoing identified publications are incorporated herein by reference and are relied on.

In accordance with one feature of the invention there is provided a new method for the synthesis of optically active amphetamines and amphetamine derivatives. In its broadest aspects the method of the invention comprises reacting an unsubstituted phenyl- or substituted phenyl acetone with an optically active methyl benzylamine to form the corresponding imine; subjecting the imine to low pressure hydrogenation conditions and subsequently forming the corresponding optically active N-(α-phenylethyl)phenylisopropylamine and subjecting the N-(α-phenylisopropylamine to hydrogenolysis. Hydrogenolysis of the N-(α-phenethyl)phenylisopropyl amines results in asymmetric optically active isomers of the general formula

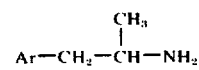

Weinges and Graab have reported an asymmetic synthesis of a methoxy-substituted amphetamine. In the Weinges and Graab procedure, 3,4-dimethoxyphenylacetone was mixed with (+)- or (−)αmethylbenzylamine and shaken at high pressures, approximately 100 atm of $H_2$, over a Raney Nickel catalyst. The subsequent and final step of the Weinges and Graab procedure required treating the resulting N-(α-phenethyl)-phenylisopropylamines to hydrogenolysis over reduced $PdCl_2$ as a catalyst. Overall yields in the Weinges and Graab reference were reportedly very low, approximately 12%. The final hydrogenolysis step required about 5 days of completion. The Weinges and Graab procedure was reported in *Chem. Ztg. Chem. App.*, 94, 728 (1970).

The method of this invention differs from the Weinges and Graab procedure in several ways. It is believed that in the course of the method of this invention an intermediate product which is an imine is formed. The imine intermediate product without being isolated is subsequently subjected, according to this invention, to a low pressure hydrogenation to produce the N-(α-phenylethyl)-phenylisopropylamines. Whereas, Weinges and Graab produce the N-(α-phenylethyl)-phenylisopropylamine in a one step high pressure hydrogenation reaction with only 20% yields. According to this invention, the N-(α-phenylethyl)-phenylisopropylamine intermediates are produced in yields of up to 70%. Moreover, this invention obviates the necessity of employing high pressure hydrogenations which are inherently dangerous.

In a somewhat simplified outline, the process of this invention comprises three basic steps, using the hydrochloride SALT as illustrative:

Step 1:

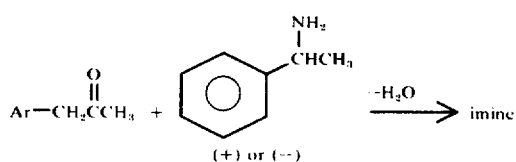

Step 2:

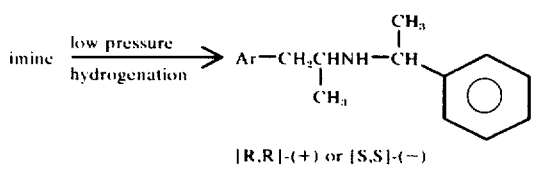

Step 3:

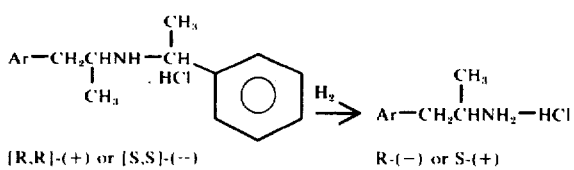

These steps will be more fully understood by the detailed description of each step in the preferred embodiment of the instant invention set forth below.

As stated above, the compounds produced by the instant invention are of the general formula

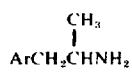

and derivatives thereof, more especially the water soluble salts thereof. These compounds are basically phenylisopropylamines. They are conventionally referred to as amphetamines and as amphetamine derivatives. The symbol "Ar" is defined as a phenyl group or as a substituted phenyl group. The selected substituents are alkyl, hydroxy or alkoxy. In particular, if the phenyl group contains alkyl substitution, the alkyl substitution will be selected from alkyl groups comprising lower alkyls. By lower alkyl is meant an alkyl group containing from 1 to 5 carbon atoms. Specifically, lower alkyl groups may be selected from methyl, ethyl, propyl, isopropyl, primary, secondary, or tertiary alkyls such as n-butyl, isobutyl or tertiary butyl. Alkoxy substituents on Ar- may be selected from the group consisting of the alkoxy groups of lower molecular weight alcohols, such as methoxy, ethoxy, propoxy and the like.

The compounds prepared by the instant invention may contain at least one oxygen substituent on the phenyl moiety or the phenyl isopropylamine, although the invention includes the preparation of unsubstituted optically active amphetamines, as can be seen from Tables I and II, compounds 1 and 1a. As can be seen from the examples in Tables I and Table II, the aromatic ring may contain dimethoxy substitution and trimethoxy substitution as well as monomethoxy substitution. In addition, the aromatic moiety of the phenylisopropylamine products may contain hydroxyl substitution. It is contemplated that any other substituent which is not labile to the reductive procedures, or which will not react with the aminoalkyl functionality present in the starting materials, may be present as substituents on the aromatic moiety of the phenylisopropylamine. Certain substituents, including halogens such as bromine, chlorine, or iodine, and sulfur compounds which may poison the catalyst, are obviously incompatible with the reaction conditions. Although such substituents may not be present in the aromatic moiety of the phenylacetone employed to produce the ultimate product, such substituents may be introduced subsequent to the formation of the desired optical isomers. Subsequent to the formation of the desired optical isomers, further chemical modifications may be carried out which will not destroy the chiral or asymmetric center producing new compounds having optical purity. By way of example, ethers may be treated to yield hydroxyls, or as another example, ether or hydroxy substituted compounds may be hydrogenated, nitrated or sulphonated to give compounds bearing substituents which could not be tolerated in the original reaction conditions for preparation of the optically active isomers. Thus, the method can indirectly lead to a wide array of optically active phenylisopropylamines.

As set forth above, the first step of the reaction process of this invention comprises reacting a phenylacetone with an optically active methylbenzyl amine. The phenylacetone has a general formula $ArCH_2(CO)CH_3$. The definition of Ar of the phenylacetone is the same as defined above with respect to the definition of the phenylisopropylamine products. Thus, Ar may contain alkyl substitution, ether substitution or hydroxy substitution. Certain substituents, enumerated above, including the halogens and sulfur compounds, which are obviously incompatible with the reaction conditions, may be introduced subsequent to the formation of the desired optically active isomers.

With respect to the examples, all of the phenylacetones employed to form the compounds in Table I have been reported in the literature with the exception of 2,5-dimethoxy4-ethyl phenylacetone, the synthesis of which is described in the experimental section. The appropriately substituted phenylacetones were either obtained commercially or prepared by Fe-HCl reduction of the corresponding 1-phenyl-2-nitropropenes, according to the Fe-HCl reduction of 1-phenyl-2-nitropropenes reported by H. Haas et al. in *J. Org. Chem.* 15, 8 (1950). The nitropropenes were prepared by condensation of the substituted benzaldehydes with EtNO$_2$, in accordance with the method and procedures published by C. B. Gairaud and G. R. Lappin, in *J. Org. Chem.*, 18, 1 (1953). All aldehydes and nitropropenes have been reported previously with the exception of the 2,5-dimethoxy-4-ethyl compounds, the synthesis of which is set forth in the experimental section.

As set forth above, step 1 of the process comprises the following reaction. In particular, a phenylacetone of the general formula, ArCH$_2$(CO)CH$_3$, where Ar is defined above, is mixed with and reacted with either (+)- or (−)-α-methyl benzylamine. (+)- and (−)-α-methylbenzylamine, employed as a reactant, may be procured from commercial sources. In particular, the reaction between the phenylacetone and the optically active methylbenzylamine includes refluxing the reaction mixture for several hours. Benzene or other solvent inert to the reaction is generally used as the reaction medium. In the course, an imine product is formed with water as a by-product. The water is removed by convenient means such as Dean-Stark trap or distillation. The imines which are believed to be formed need not be isolated. However, it is contemplated that isolation of the imines may be an optional step. The appropriate phenylacetone and optically active α-methylbenzylamine are usually allowed to reflux for a period of 24 hours with continuous water removal. The formation of the imine intermediate, according to this invention, is distinct from Weinges and Graab method.

In the Weinges and Graab method, the imine is formed and hydrogenated at the same time. Low yields are obtained. In the method of this invention the water formed in the reaction is removed and the imine intermediate is then treated to low pressure hydrogenation. Particularly, the resulting imines, which were not isolated, were reduced directly at 50 psig in a Parr shaker. The resulting optically active N-(α-phenethyl)-phenylisopropylamines are actually reduction products of the preformed imines. In a preferred embodiment, the low pressure hydrogenation includes as a reducing agent, hydrogen gas at, for example, 50 psig. in the presence of a Raney-Nickel catalyst.

In a preferred embodiment, the method of this invention includes the further treatment of the resultant N-(α-phenethyl)-phenylisopropylamine with acid to form the corresponding acid salt salt.

In the hydrogenation step 2, the imine will absorb the calculated amount of hydrogen within about 24 hours to produce the resultant optically active N-(α-phenethyl)phenylisopropylamine. The reduction of the imine is usually undertaken in a protic solvent. After hydrogen uptake ceases, the solvent containing the reduced product is filtered. The filtrate is then acidified. Acidification results in the formation of the salt of the optically active N-(α-phenethyl)phenylisopropylamine. Usually, acidification is undertaken with a solution of an acid and the solvent employed to conduct the Raney Nickel reduction of the imines of step 1. Ethanol is often employed as a solvent medium for the Raney-Nickel reduction of imine. Thus, acidification may be conducted with a solution of ethanol and acid. Although various mineral acids may be employed, hydrochloric acid has been found to be particularly useful. In this embodiment, the hydrochloric acid salt of the N-(α-phenethyl)phenylisopropylamine is the ultimate product of Step 2.

When the hydrochloride salt is formed, it may be precipitated by dilution of the acidified solvent medium with ethyl ether. Re-crystallization of the hydrochloride salt of the amine product of step 2 may be conducted with various mixtures of solvents. Particularly, recrystallization may be undertaken with an acetone water-solvent solution or with an acetone-isopropanol solvent mixture.

Step 3 comprises the hydrogenolysis of the N-(α-phenethyl)phenylisopropylamine to form the ultimate products of the instant invention, optically active substituted phenylisopropylamines. In the illustration above, the hydrochloride salts of the N-(α-phenethyl)-phenylisopropylamines are employed in the hydrogenolysis of step 3. The hydrogenolysis of step 3 proceeds in quantitative yields and usually occurs in less than 36 hours when a 10% Pd/C catalyst is employed. Generally this reaction is undertaken in a solvent. It was found convenient and efficient to employ methanol as a solvent for hydrogenolysis of the N-(α-phenethyl)-phenylisopropylamine hydrochlorides over a Pd/C catalyst.

The summary of the data relating to the ultimate optically active phenylisopropylamine produced by the instant invention is set forth in Table II. Highest enantiomer purity was obtained by several recrystallizations of the N-(α-phenethyl)-phenylisopropylamines. Such a fact indicates that final purity is dependent on the purity of the diastereomeric intermediates. However, a single recyrstallization sufficed to give enantiomeric purities of final compounds in the range of 96 to 97%.

TPC amide (N-trifluoroacetyl-S-prolylamides) derivatives were used to confirm the absolute configuration of the resulting products. Westley, et al., in *Anal. Chem.*, 10, 2046 (1968), pointed out that the S,S diastereomer of N-trifluoroacetyl-S-prolylamides always elutes after the S,R form. Although stereospecificity of the asymmetric synthesis is strong presumptive evidence for predicting the absolute configuration of the enantiomers, the order of elution of the TPC amides confirms that in every case the compounds which were produced were of the R-(−) and the S-(+) configurations.

Glc analysis of enantiomer purity using the α-methoxy-α-trifluoromethylphenyl acetamides (MTPA amides), indicated that retention times were in the order of 20 to 30 minutes with typical separation between diastereomers of 4 to 6 minutes. The (−)-amine-(+)-MTPA or (+)-amine-(−)-MTPA amides have longer retention times than the (−)-amine-(−)-MTPA or (+)-amine-(+)-MTPA amides. Dale, et al., have presented evidence suggesting that MTPA is of the R-(+) absolute configuration. If such assignment is correct, the order of elution of the diastereomers if R,S or S,R before R,R or S,S. Such a result would be apparently consistent with the findings of Westley et al. set forth above.

Attempts to employ N-trifluoroacetyl-S-prolylamides (TPC amides) to determine enantiomer purity were complicated by racemization of the reagent. Although TPC reagent is inexpensive and has been used to determine the enantiomeric purity of amphetamines in the past, variable results were obtained in attempting to determine the enantiomeric purity of the substituted amphetamines because of racemization during the preparation of the amides. As a control, (−)-α-methylbenzylamines of known (99+%) enantiomeric purity was tested in this fashion and was found to lose apparent purity which varied from 85 to 95%. The variation in the apparent purity appeared to be related to the length of time the amide preparations were allowed to stand before work-up. Although the exact reason for the racemization of the TPC derivatives is not known, it is possible that in the presence of amines racemization would proceed through a ketene intermediate. Thus, it is more reliable to use the MTPA amides in which no possibility of racemization exists to determine enantiomeric purity.

Employing the method described by Dale et al. in *J. Org. Chem.*, 34, 2543 (1969), the enantiomeric purity of isomers was also determined by fluorine nmr. The data so obtained is set forth in Table III in the experimental section. Analysis by this method indicated that the purity of the compounds appeared to be 100%, whereas, glc analysis indicated that such a value was too high.

Molar rotations for the phenylisopropylamines were calculated and are set forth in Table II, which is contained in the experimental section. The data appears to indicate that [ α ] D for the 2,5-dimethoxy-substituted series depends only on the atomic weight of the para-substituent. An attempt to extend this method to preparation of enantiomers of 2-aminotetralin resulted in optical purity of only 5 to 10%. Moreover, the enantiomers of 1,2,3,4-tetrahydro-2-naphthylamine could not be prepared by this method.

EXPERIMENTAL

Melting points were determined in open glass capillaries using a Thomas-Hoover Uni-Melt apparatus and were corrected. Elemental analyses were undertaken by Midwest Microlab, Ltd., Indianapolis, Inc., or by the Microanalytical Laboratory of the Division of Medicinal Chemistry, University of Iowa. Where analyses are indicated by symbols of the elements, the analytical results obtained were within ±0.4% of the calculated values. Optical rotations were measured with a Perkin-Elmer Model 141 polarimeter using 2% solutions in MEOH or $H_2O$ as indicated. Glc analyses were performed on a Hewlett-Packard Model 5750 gas chromatograph equipped with a flame ioniztion detector. Fluorine nmr were run on a Varian Associates HA-100 spectrometer (94.1 MHz). Chemical shifts were measured in 80% $CDCl_3$ relative to an internal standard of 20% $CF_3COOH$.

EXAMPLES 1 THROUGH 14

The compounds set forth in Table I are typically prepared according to the following method.

[R;R]-(+) or [S;S]-(−) Substituted N-(α-phenethyl)-phenylisopropylamine hydrochlorides Step 1:

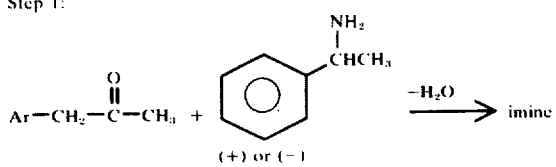

The appropriate phenylacetone, 0.05 moles, and 0.05 M of either R-(+) or S-(−)α-methylbenzylamine (Aldrich) were heated together under reflux in 50 ml $C_6H_6$ for 24 hours with continuous $H_2O$ removal. Addition of a few drops of AcOH did not decrease reaction time. The $C_6H_6$ were removed.

Step 2:

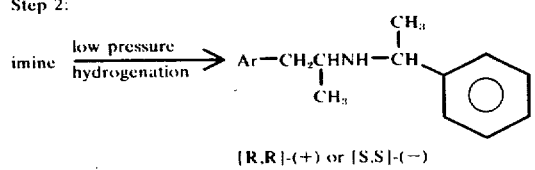

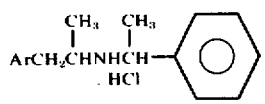

After the benzene was removed, the residue was dissolved in 50 ml abs EtOH and the resulting solution shaken over 2.g. EtOH-washed W-2 Ra-Ni at 50 psig. $H_2$ until the calculated amount of $H_2$ was absorbed, usually within 24 hours. The mixture was filtered through sintered glass, ± the filtrate acidified with EtOH-HCl and concentrated to small volume. The HCl salt precipitated upon dilution with $Et_2O$ and was recrystallized from $Me_2CO$-$H_2O$ or $Me_2CO$-isoPrOH.

± The catalyst is extremely pyrophoric.

The compounds resulting from Step 2 are set forth in Table 1.

TABLE I

Substituted N-(α-Phenethyl)phenylisopropylamine Hydrochlorides

ArCH₂CHNHCH-C₆H₅ · HCl (CH₃, CH₃)

| Compd | Ar substitution | Isomer | [α]D, deg (c 2, MeOH) | Mp, ° C (cor) | Yield, % | Formula | Analyses |
|---|---|---|---|---|---|---|---|
| 1 | Unsubstituted | R,R-(+) | +21.0 | 233.5–234.5 | 70.5 | $C_{17}H_{22}ClN$ | C,H,N |
| 2 | 3,4-(OMe)₂ | S,S-(−) | −20.5 | 216–217 | 48 | $C_{19}H_{26}ClNO_2$ | C,H,N |
| 3 | 4-OMe | R,R-(+) | +36.1 | 195–197 | 40 | $C_{18}H_{24}ClNO$ | C,H,N |
| 4 | 4-OMe | S,S-(−) | −36.1 | 195–197 | 57.5 | $C_{18}H_{24}ClNO$ | C,H,N |
| 5 | 2,3-(OMe)₂ | R,R-(+) | +22.1 | 181–182 | 32 | $C_{19}H_{26}ClNO_2$ | C,H,N |
| 6 | 2,3-(OMe)₂ | S,S-(−) | −21.7 | 180–181 |  | $C_{19}H_{26}ClNO_2$ | C,H,N |
| 7 | 2,5-(OMe)₂ | R,R-(+) | +7.50 | 227–228 | 63 | $C_{19}H_{26}ClNO_2$ | C,H,N |
| 8 | 2,5-(OMe)₂ | S,S-(−) | −7.75 | 227–228 | 67 | $C_{19}H_{26}ClNO_2$ | C,H,N |
| 9 | 3,4,5-(OMe)₃ | R,R-(+) | +4.00 | 223–224.5 | 67 | $C_{20}H_{28}ClNO_3$ | C,H,Cl |
| 10 | 3,4,5-(OMe)₃ | S,S-(−) | −4.24 | 223.5–224.5 | 68 | $C_{20}H_{28}ClNO_3$ | C,H,Cl |
| 11 | 2,5-(OMe)₂-4-Me | R,R-(+) | +7.38 | 198–199 | 44 | $C_{20}H_{28}ClNO_2$ | C,H,Cl |
| 12 | 2,5-(OMe)₂-4-Me | S,S-(−) | −7.18 | 195–196.5 | 41 | $C_{20}H_{28}ClNO_2$ | C,H,Cl |
| 13 | 2,5-(OMe)₂-4-Et | R,R-(+) | +11.2 | 214–214.5 | 40 | $C_{21}H_{30}ClNO_2$ | C,H,N |
| 14 | 2,5-(OMe)₂-4-Et | S,S-(−) | −11.4 | 213.5–214.5 | 24 | $C_{21}H_{30}ClNO_2$ | C,H,N |

EXAMPLES 1a THROUGH 14

The ultimate products, set forth in Table 2, and resulting from Step 3:

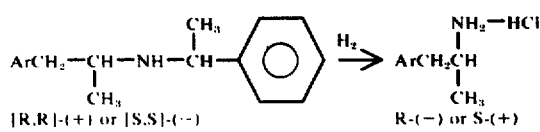

$[R;R]-(+)$ or $[S;S]-(-)$     $R-(-)$ or $S-(+)$ may be prepared according to the following procedure.

R-(−) or S-(+) Substituted Phenylisopropylamine Hydrochlorides

To a slurry of 0.35 g of 10% Pd-C in several ml of $H_2O$ was added 90 ml of MeOH and 5 g of either the $[R;R]-(+)$ or $[S;S]-(-)$ N-($\alpha$-phenethyl)phenylisopropylamine HCl prepared above. The mixture was shaken at 50 psig $H_2$. The calculated uptake usually occurred within 48 hours (reduced amounts of catalyst greatly prolonged this time). The mixture was filtered, concentrated to dryness and the residue recrystallized from isoPrOH-$Et_2O$.

TABLE II

SUBSTITUTED PHENYLISOPROPYLAMINE HYDROCHLORIDES $$ArCH_2\overset{CH_3}{\underset{|}{C}}HNH_2 \cdot HCl$$

| Compd | Ar Substitution | Isomer | $\|\alpha\|^{25}D$, deg (c2, $H_2O$) | $\|M\|D\|$ | Mp.° C(cor) |
|---|---|---|---|---|---|
| 1a | Unsubstituted | R-(−) | −27.2[b] | 46.7 | 157–158 |
| 2a | 3,4-(OMe)₂ (3,4-DMA) | S-(+) | +23.1[c] | 53.5 | 141–142 |
| 3a | 4-OCH₃(PMA) | R-(−) | −22.5 | 45.4 | 251–253 |
| 4a | 4-OCH₃ | S-(+) | +22.4 | 45.2 | 250.5–251.5 |
| 5a | 2,3-(OMe)₂ (2,3-DMA) | R-(−) | −16.9 | 39.2 | 124–125 |
| 6a | 2,3-(OMe)₂ | S-(+) | +16.6 | 38.5 | 123–124 |
| 7a | 2,5-(OMe)₂ (2,5-DMA) | R-(−) | −18.7 | 43.3 | 145–146 |
| 8a | 2,5-(OMe)₂ | S-(+) | +18.0 | 41.7 | 144–145 |
| 9a | 3,4,5-(OMe)₃ (TMA) | R-(−) | −17.7 | 46.3 | 206–208 |
| 10a | 3,4,5-(OMe)₃ | S-(+) | +17.3 | 45.3 | 206–208 |
| 11a | 2,5-(OMe)₂-4-Me (DOM) | R-(−) | −17.2 | 42.3 | 204–205 |
| 12a | 2,5-(OMe)₂-4-Me | S-(+) | +17.2 | 42.3 | 204–205 |
| 13a | 2,5-(OMe)₂-4-Et (DOEt) | R-(−) | −16.1 | 41.8 | 226.5–227 |
| 14a | 2,5-(OMe)₂-4-Et | S-(+) | +16.0 | 41.6 | 225.5–226.5 |
| 15 | 2,5-(OMe)₂-4Br (DOB) | R-(−) | −13.7 | 42.5 | 203.5–204 |
| 16 | 2,5-(OMe)₂-4-Br | S-(+) | +13.7 | 42.5 | 204–205 |

[a]Quantitative yields of slightly depressed melting points are obtained; reported yields are recrystallized.
[b]$[\alpha]D$ 24.8°; W. Leithe, Chem. Ber., 65,664 (1932).
[c]Lit.²⁵$[\alpha]D$ 23°.
[d]Determined by glc analysis of MTPA amines.
[e]Determined by fluorine nmr of MTPA amines.
[f]Yields based on 2,5-DMA starting material.

TABLE II

SUBSTITUTED PHENYLISOPROPYLAMINE HYDROCHLORIDES

| Compd | % yield[a] | Enantiomer purity, % | Formula |
|---|---|---|---|
| 1a | 83 | 100[e] | C₉H₁₄ClN |
| 2a | 90 | 97[d] | C₁₁H₁₈ClNO₂ |
| 3a | 62 | 99,[d]100[e] | C₁₀H₁₆ClNO |
| 4a | 68 | | C₁₀H₁₆ClNO |
| 5a | 92 | 97[d] | C₁₁H₁₈ClNO₂ |
| 6a | 90 | | C₁₁H₁₈ClNO₂ |
| 7a | 87 | 96,[d]100[e] | C₁₁H₁₈ClNO₂ |

TABLE II-continued

SUBSTITUTED PHENYLISOPROPYLAMINE HYDROCHLORIDES

| Compd | % yield[a] | Enantiomer purity, % | Formula |
|---|---|---|---|
| 8a | 90 | 96[d] | C₁₁H₁₈ClNO₂ |
| 9a | 84 | | C₁₂H₂₀ClNO₃ |
| 10a | 82 | | C₁₂H₂₀ClNO₃ |
| 11a | 83 | 96[d] | C₁₂H₂₀ClNO₂ |
| 12a | 82 | | C₁₂H₂₀ClNO₂ |
| 13a | 97 | 99[d] | C₁₃H₂₂ClNO₂ |
| 14a | 97 | 97[d] | C₁₃H₂₂ClNO₂ |
| 15 | 54.5[f] | | C₁₁H₁₇BrClNO₂ |
| 16 | 54.5[f] | 100[e] | C₁₁H₁₇BrClNO₂ |

[a]Quantitative yields of slightly depressed melting points are obtained; reported yields are recrystallized.
[b]$[\alpha]D$ 24.8°; W. Leith, Chem. Ber., 65,664 (1932).
[c]Lit.²⁵$[\alpha]D$ 23°.
[d]Determined by glc analysis of MTPA amines.
[e]Determined by fluorine nmr of MTPA amines.
[f]Yields based on 2,5-DMA starting material.

EXAMPLES 15 and 16

As set forth above, the Ar group of the reactant $ArCH_2(CO)CH_3$ should not contain substituents which would interfere with the reaction conditions of Step 1, Step 2 or Step 3. Such substituents, which might interfere with the reaction conditions of the instant process may be introduced into an Ar-moiety after the production of the ultimate optically active phenylisopropylamines are synthesized. The following example shows the method of introducing a bromine atom into the Ar-moiety to produce compounds 15 and 16 as set forth in Table II.

(+) or (−) 2,5-Dimethoxy-4-bromoamphetamine hydrochloride

Bromination was accomplished by the method of Harley-Mason published in *J. Chem. Soc.*, 200 (1953). The free base, (1.62 g; 8.3 mM), of either (+) or (−), 2,5-DMA was dissolved in 6 ml AcOH. A solution of 1.33 g (8.3 mM) of $Br_2$ in 4.5 ml AcOH was added over 10 minutes and the solution stirred 24 hours at room temperature. The mixture was diluted to 200 ml with $Et_2O$ and the HBr salt precipitated. The salt was collected by filtration, neutralized with 10% NaOH, taken up into $Et_2O$ and precipitated as the HCl salt with dry HCl. The salt was recrystallized from isoPrOH. Yield 1.40 g (54.5%).

EXAMPLE 17

Preparation of 2,5-dimethoxy-4-ethyl-phenylacetone 2,5-dimethoxy-4-ethylbenzaldehyde. This was prepared by a modification of the method of Rieche, et al. in *Org. Syn*, 47, 1 (1967). 2,5-dimethoxyethylbenzene(66.4 g, 0.4 mol) was dissolved in 250 ml of dry $CH_2Cl_2$ and cooled to 10° and 208 g (0.8 mol) of anhydrous $SnCl_4$ was added. $Cl_2CHOCH_3$ (45.9 g, 0.4 mol) was then added over 40 minutes, maintaining the temperature at 5° – 10°. The preparation of 2,5-dimethoxyethylbenzene was reported by Howe, et al. *J. Org. Chem*, 25 1245 (1960). The solution was allowed to warm to room temperature over 45 minutes, heated under reflux for 1 hour, cooled, and poured over 500 g of ice-$H_2O$. The aqueous layer was discarded. The $CH_2Cl_2$ layer was washed with 3 N HCl and $H_2O$ and dried ($Na_2SO_4$). After removal of the solvent the residue was triturated with saturated $NaHSO_3$ solution. The addition product was dissolved in $H_2O$; the aqueous solution was washed with $Et_2O$ and then decomposed with $Na_2CO_3$ solution. On cooling, the aldehyde solidified, was collected by filtration, and recrystallized from MeOH-$H_2O$: yield 42 g (54%); mp 46° – 47°. Anal. ($C_{11}H_{14}O_3$)C, H.

1-(2,5-dimethoxy-4-ethylphenyl)-2-nitropropene was prepared by condensation of the above aldehyde with $EtNO_2$ in AcOH containing $NH_4OAc$, according to C. B. Gairand and G. R. Lappin procedure in *J. Org. Chem.*, 15, 8 (1953). The yellow product was recrystallized from MeOH: yield 60.8%; mp 63° – 64°. Anal. ($C_{13}H_{17}NO_4$) C, H, N.

1-(2,5-dimethoxy-4-ethylphenyl)-2-propanone. This substituted phenylacetone was prepared by Fe-HCl reduction of the above nitro compound by the method of Haas: yield 60%; bp 131° – 132° (0.1 mm); characterized as the oxime, mp 79.5° – 80.5°. Anal. ($C_{13}H_{19}NO_3$) C, H, N.

Identification Procedures

Preparation of MTPA Amides.

In accordance with the postulates set forth by Dale et al. in *J. Org. Chem.*, 34, 2543 (1969) the MTPA amides were prepared.

(+)- or (−)-methoxytrifluoromethylphenylacetic acid (MTPA, Aldrich) (1 g) was refluxed 12 hr with 10 ml of $SOCl_2$. The $SOCl_2$ was removed and the MTPA-Cl diluted with 1 ml of dry pyridine and 4.6 ml of $CHCl_3$. The amphetamine HCl (0.5 mmol) was dissolved in 0.25 ml of pyridine and 0.5 ml of $CHCl_3$ and allowed to sit overnight with one-fourth of the MTPA-Cl solution (approximately 1.05 mmol). The solution was diluted to 10 ml with $CHCl_3$ and washed with 3 N HCl, 4% $NaHCO_3$, and $H_2O$. The $CHCl_3$ solution was dried ($NaSO_4$), the $CHCl_3$ removed, and the residue recrystallized from $C_6H_6$-hexane. This was difficult in most cases and analyses were usually carried out on the crude viscous amide.

Glc Analysis of MTPA Amides.

A copper column, 1.33 m × 3.18 mm i.d., packed with 2% Carbowax 20M on 80 – 100 mesh Gas Chrom Q (Applied Science Labs) was used. The column was conditioned for 24 hours at 225° before use and operated at the same temperature. The He carrier gas flow was adjusted to ca. 100 ml/min. Sample and detector temperatures were set at 300°. A 5-μ l volume containing 5-10 μg of the MTPA amide was injected and the per cent composition determined by cutting out the peaks and integrating the area by direct weighing.

Preparation of N-Trifluoroacetyl-S-prolylamides and Determination of Absolute Configuration The N-trifluoroacetyl-S-prolyl chloride reagent was prepared in accordance with the Weygand, et al., procedure, in *Chem.. Ber.*, 90, 1896 (1957) or according to the Wells method published in *J. Off. Ass. Anal. Chem.*, 55, 146 (1972). (TPC reagent is available from Regis Chemical Co.) Amides of the amphetamine isomers were prepared and analyzed using the same column and conditions as was described for the MTPA amides. Table III. Nmr Chemical Shifts of Diasteromeric Amides of (+)- or (−)-α-methoxy-α-trifluoromethylphenylacetamides

| Diastereomer | Amine configuration | Chemical shifts of diastereomers of Hz downfield of trifluoroacetic acid |
|---|---|---|
| (−)-Amphetamine (+)-MTPA | R | 687 |
| (−)-p-Methoxyamphetamine (+)-MTPA | R | 686 |
| (−)-2,5-Dimethoxy-amphetamine (−)-MTPA | R | 675 |
| (+)-2,5-Dimethoxy-4-bromoamphetamine (+)-MTPA | S | 660 |

The results noted above have been previously reported in the Journal of Medicinal Chemistry, Vol. 16, 480–483 (1973), and that article is incorporated herein.

What is claimed is:

1. A method of preparing the R-(−) and S-(+) isomers of a compound of the general formula

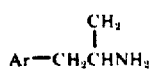

or water soluble salts thereof wherein Ar is an unsubstituted phenyl group or a phenyl group substituted by lower alkyl, lower alkoxy, hydroxy or a mixture thereof wherein the method comprises a. mixing a phenyl acetone compound of the formula:

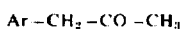

wherein Ar is as defined above, with an optically active methyl benzyl amine to form a reaction mixture and reacting at elevated temperature, b. removing at least a portion of the water produced in the reaction, c. and thereafter subjecting the reaction mixture under reducing conditions to low pressures of hydrogen gas in the presence of a hydrogenation catalyst to produce a corresponding optically active N-(α-phenylethyl)phenylisopropylamines, d. recrystallizing the N-(α-phenylethyl)phenylisopropylamines, and e. subjecting said optically active amine to hydrogenolysis.

2. The method of claim 1, wherein step (a) comprises refluxing Ar—CH$_2$(CO—)CH$_3$ with said optically active methyl benzyl amine.

3. The method of claim 1, wherein step (c) is undertaken at a pressure in the range of 30–150 psig.

4. The method of claim 3, wherein the hydrogenation conditions include a Raney-Nickel catalyst.

5. The method of claim 1, wherein the hydrogenation of step (d) includes a Pd/C catalyst.

6. The method of claim 1, wherein step (c) further includes the step of acidifying the amine product step (c) to form the corresponding acid salt.

7. The method of claim 3, wherein step (c) further includes the step of acidifying the amine product of step (c) to form the corresponding acid salt.

8. The method of claim 7, wherein the hydrogenolysis of step (d) is performed using a Pd/Catalyst.

9. The method of claim 8 wherein step (d) is performed employing a water-methanol medium.

10. The method of claim 1, wherein Ar is unsubstituted.

11. The method of claim 1, wherein Ar is 3,4-dimethoxy substituted.

12. The method of claim 1, wherein Ar is 4-methoxy substituted.

13. The method of claim 1, wherein Ar is 2,3-dimethoxy substituted.

14. The method of claim 1, wherein Ar is 2,5-dimethoxy substituted.

15. The method of claim 1, wherein Ar is 2,5-dimethoxy-4-methyl substituted.

16. The method of claim 1, wherein Ar is 2,5-dimethoxy-4-ethyl substituted.

17. The method of claim 1, which includes as a final step, subjecting optically active phenylisopropylamines to an aromatic substitution reaction of halogenation thereby introducing into the Ar moiety substituents which are labile to the reaction conditions of steps (a), (b), (c) and (d).

18. The method of claim 1, which includes the step of reacting the optically active phenylisopropylamines, wherein Ar contains ether substitution, with an ether cleavage reagent.

19. The method of claim 17 wherein (+)- or (−)-2,5-dimethoxyamphetamine is treated with Br$_2$ in the presence of a solvent.

20. A method of preparing the R-(−) and S-(+) isomers of a compound of the general formula

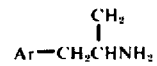

or water soluble salts thereof wherein Ar is an unsubstituted phenyl group or a phenyl group substituted by lower alkyl, lower alkoxy, hydroxy or a mixture thereof wherein the method comprises a. mixing a phenyl acetone compound of the formula

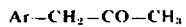

wherein Ar is as defined above, with an optically active methyl benzyl amine to form a reaction mixture and reacting at elevated temperature, b. removing at least a portion of the water produced in the reaction, c. and thereafter subjecting the reaction mixture under reducing conditions to low pressures of hydrogen gas in the presence of a hydrogenation catalyst to produce a corresponding optically active N-(α-phenylethyl)phenylisopropylamines, filtering and then acidifying the filtrate, d. recrystallizing the N-(α-phenylethyl)phenylisopropylamines in a solvent, and e. subjecting said optically active amine to hydrogenolysis.

21. The method of claim 20 wherein a plurality of recrystallizations are conducted in step (d).

22. A method of preparing the R-(−) and S-(+) isomers of a compound of the general formula

or water soluble salts thereof wherein Ar is an unsubstituted phenyl group or a phenyl group substituted by lower alkyl, lower alkoxy, hydroxy or a mixture thereof wherein the method comprises a. mixing a phenyl acetone compound fo the formula

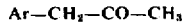

wherein Ar is as defined above, with an optically active methyl benzyl amine to form a reaction mixture and reacting at elevated temperature, b. removing at least a portion of the water produced in the reaction, c. and thereafter subjecting the reaction mixture under reducing conditions to low pressures of hydrogen gas in the presence of a Raney-Nickel hydrogenation catalyst and a solvent for the reaction to produce a corresponding optically active N-(α-phenylethyl)phenylisopropylamines, filtering and acidifying the filtrate to obtain an acid salt, d. adding ethyl ether and recrystallizing the acid salt of N-(α-phenylethyl)phenylisopropylamines, and e. subjecting said acid salt of the optically active amine to hydrogenolysis.

* * * * *